US009050061B2

(12) United States Patent
Omoda

(10) Patent No.: US 9,050,061 B2
(45) Date of Patent: Jun. 9, 2015

(54) HEALTH CARE DEVICE WITH A SAMPLE CAPTURE SYSTEM TO EVALUATE A HEALTH CONDITION

(75) Inventor: Ryo Omoda, Kyoto (JP)

(73) Assignee: EMPIRE TECHNOLOGY DEVELOPMENT LLC, Wilmington, DE (US)

(*) Notice: Subject to any disclaimer, the term of this patent is extended or adjusted under 35 U.S.C. 154(b) by 1030 days.

(21) Appl. No.: 12/550,629

(22) Filed: Aug. 31, 2009

(65) Prior Publication Data

US 2011/0054273 A1    Mar. 3, 2011

(51) Int. Cl.

| | |
|---|---|
| *A61B 5/05* | (2006.01) |
| *A61B 5/00* | (2006.01) |
| *A61B 5/117* | (2006.01) |
| *A61B 5/145* | (2006.01) |
| *A61B 10/00* | (2006.01) |
| *G01N 33/497* | (2006.01) |

(52) U.S. Cl.
CPC ............ *A61B 5/6891* (2013.01); *G01N 33/497* (2013.01); *A61B 5/117* (2013.01); *A61B 5/145* (2013.01); *A61B 5/4266* (2013.01); *A61B 5/4272* (2013.01); *A61B 5/4277* (2013.01); *A61B 10/0064* (2013.01)

(58) Field of Classification Search
CPC .. A61B 5/6887; A61B 5/6888; A61B 5/6889; A61B 5/6891; A61B 5/6892; A61B 5/6893; A61B 5/6894; A61B 5/6895; A61B 5/6896; A61B 5/6897; A61B 5/6898; A61B 2010/0083; A61B 5/117; B60W 2540/00; B60W 2540/24; B60W 2540/22; B60W 2540/26; G01N 33/497

USPC ......... 600/306, 307, 308, 309, 310, 316, 317, 600/345–347, 352, 362, 365; 607/58
See application file for complete search history.

(56) References Cited

U.S. PATENT DOCUMENTS

| | | | |
|---|---|---|---|
| 5,757,278 A | 5/1998 | Itsumi | |
| 5,969,615 A * | 10/1999 | Ivey et al. | ...................... 340/576 |
| 6,229,908 B1 * | 5/2001 | Edmonds et al. | ............. 382/124 |
| 7,383,072 B2 | 6/2008 | Edmonson et al. | |

(Continued)

FOREIGN PATENT DOCUMENTS

WO    2005/098429 A2    10/2005

OTHER PUBLICATIONS

PharmChek® Drugs of Abuse Patch, accessed at http://web.archive.org/web/20090103111118/http://www.pharmchem.com/Products/Patch_details.htm, accessed on May 17, 2012, 2 pages.

(Continued)

*Primary Examiner* — Navin Natnithithadha
*Assistant Examiner* — Eric Messersmith
(74) *Attorney, Agent, or Firm* — Workman Nydegger

(57) ABSTRACT

Embodiments described herein relate to health monitoring apparatuses, systems and methods that allow a user to passively monitor her/his health. Embodiments include acquiring chemical substances from a subject's skin (e.g., in sweat and/or sweat vapor or oil excretions) using a sample capture system located on a mounting portion in a fixed location. Embodiments also include analyzing chemical substance(s) acquiring from the subject's skin to generate raw data. Embodiments further include analyzing the raw data to generate health status data for a particular subject.

19 Claims, 4 Drawing Sheets

(56) References Cited

U.S. PATENT DOCUMENTS

| | | | |
|---|---|---|---|
| 7,911,350 B2* | 3/2011 | Shoji et al. | 340/576 |
| 2006/0202842 A1* | 9/2006 | Sofer | 340/576 |

OTHER PUBLICATIONS

"Drug Testing Technologies: Sweat Patch," accessed at http://web.archive.org/web/20090816165916/http://www.drugpolicy.org/law/drugtesting/sweatpatch_/, accessed on May 17, 2012, 5 pages.

Hunka, G., "TAU Chemists Explore Sweat as the Fingerprint of the Future," accessed at http://web.archive.org/web/20090225062348/http://www.medicalnewstoday.com/articles/139598.php, Feb. 19, 2009, 3 pages.

Wikipedia, Author Unknown, "Immunoglobulin A", accessed Jun. 11, 2012.

Schittek, et al., "Dermcidin: a Novel Human Antibiotic Peptide Secreted by Sweat Glands", Nature Immunology, vol. 2 No. 12, Dec. 2001, pp. 1133-1137.

Murphy, "Blood, sweat, and chemotactic Cytokines" Journal of Leukocyte Biology, vol. 57, Mar. 1995, pp. 438-439.

Chien-Tsai Huang, et al "Uric Acid and Urea in Human Sweat" Chinese Journal of Physiology, 45(3): 109-115, 2002.

Gian Luca Marcialis, et al "Fingerprint verification by fusion of optical and capacitive sensors" Pattern Recognition Letters, 25 (2004) 1315-1322.

Michael Goh Kah Ong, et al "A Single sensor Hand Geometry and Palmprint Verification System" International Multimedia Conference archive: Proceedings of the 2003 ACM SIGMM workshop on Biometrics methods and applications, pp. 100-106 (2003).

Aronon Amir, et al "An embedded system for an eye-detection sensor" Computer Vision and Image Understanding 98 (2005) 104-123.

Online: http://health.goo.ne.jp/special/summer/sweat/index2.html.

\* cited by examiner

HEALTH CARE DEVICE WITH A SAMPLE CAPTURE SYSTEM TO EVALUATE A HEALTH CONDITION

TECHNICAL FIELD

Embodiments described herein relate to health monitoring apparatuses, systems and methods that allow a user to passively monitor her/his health.

BACKGROUND

Various techniques exist to evaluate a person's health condition. Generally, these include evaluating levels of various substances in a person's blood, urine, saliva, sweat or other bodily fluids and/or tissue. There are many markers in blood known to indicate various health conditions. For example, high levels of urea/uric acid can indicate gout, chroline can indicate pancreatitis, and lactase can indicate respiratory failure. Techniques for evaluating a person's health condition can in some cases be quite invasive and may require a person to travel to a clinic/hospital to have a bodily sample taken, such as blood sample, urine sample, saliva sample, sweat sample, biopsy, and the like. Not only does this take time, but also creates inconvenience for the person. It would be desirable to improve techniques for monitoring a person's health.

DETAILED DESCRIPTION

Figure 1A:
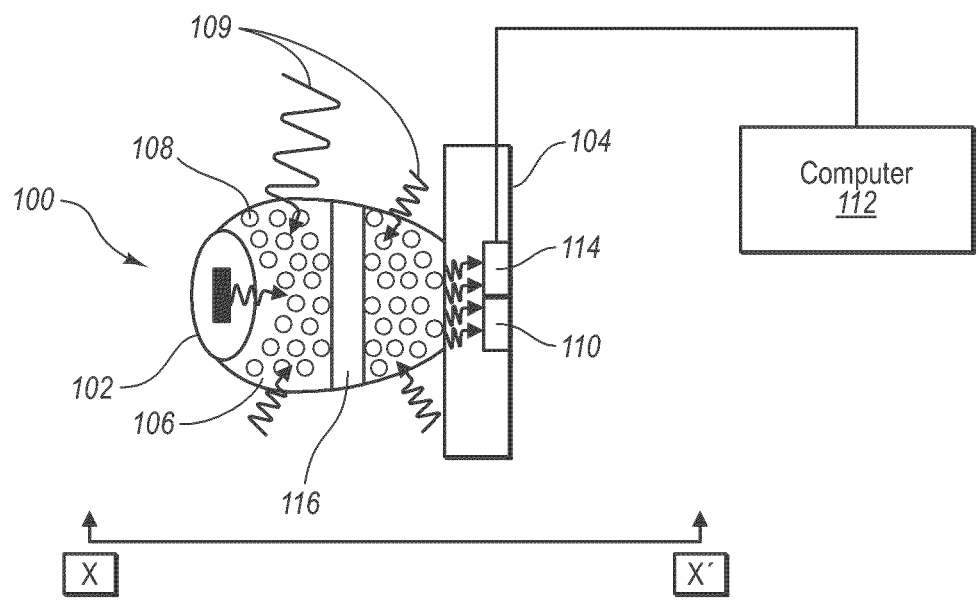
FIG. 1A is a schematic view of an illustrative embodiment of an apparatus of this disclosure.

In the following detailed description, reference is made to the accompanying drawings, which form a part hereof In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The ability to monitor a person's health condition has been the subject of various developing technology. As used herein, the term "subject" will refer broadly to a person, although does not have to be the same person each time the technology is used. Further, a "subject" does not have to be a human being, but may be another animal being monitored for health conditions, such as a dog, cat, monkey, or any other animal that can be trained to repeatedly come in contact with the health care device disclosed herein.

There are various indicative chemical substances that are excreted from human's or animal's skin. Various types of substances can be excreted from a subject's skin. For example, a human's sudoriferous glands excrete water and/or chemicals in a person's sweat excretions and/or sweat vapor. In another example, a human's sebaceous gland excretes oil and/or chemicals from a person's skin. It is not uncommon for the excretions from sweat glands or oil glands to combine since different types of glands are located in close proximity with each other. The type of excretions will depend on the subject that is monitored (i.e., human or animal), but generally, embodiments herein are able to collect and monitor chemical substances in discrete sampling events in a passive manner that is noninvasive to the subject.

The disclosure provides apparatuses, systems and methods for monitoring a subject's health using a simple device and sensor. Further, the apparatus is mounted in an accessible location where it is easy for a subject to come into contact with the apparatus without requiring the subject to inconvenience themselves to find the apparatus. In one embodiment, the apparatus is fashioned and implemented as a door knob, providing easy periodic monitoring that occurs as the subject goes about her/his daily business, without active thought required by the subject to use the apparatus. Depending on the placement of the doorknob sensor, monitoring can occur more or less frequently as desired such as frequently throughout the day, daily, weekly, and any other various timings. Further, depending on the placement of the doorknob sensor, multiple subjects can be monitored which may only require a minor identification process. In another embodiment, the apparatus is mounted on a door jamb, on a wall, on a chair, on a table, or any other location that is frequently contacted by the subject. In still another embodiment, the apparatus can be mounted low to the ground so that the health of other subjects, such as a pet, can be frequently monitored. For example, the apparatus can be mounted inside a pet door so that when the pet rubs against the apparatus, the apparatus is able to collect a chemical sample. In another embodiment, a pet can be trained to rub against the apparatus mounted by, for example, the pet's litter box or food/water station. Other embodiments are possible in view of the disclosure herein.

Generally, the apparatus is mounted to a fixed location. The examples described above indicate that the term "fixed location" is used to refer to the direct mount upon which the apparatus is mounted, which is fixed as opposed to having the apparatus be mobile and carried around by the subject. The term "fixed location" is used to refer to a location with which the user comes in regular contact. However, the fixed location itself may be moveable. For example, the doorknob embodiment is movable to operate a door between an open and closed state. The doorknob itself, however, is in a fixed location so that the subject comes into regular, repeated contact with the doorknob.

FIG. 1A is a schematic view of the apparatus of this disclosure. One of the aspects of this disclosure provides an apparatus for monitoring health, the apparatus having a sample capture system configured to collect at least some chemicals excreted from a skin surface of a subject, wherein the sample capture system is configured for installation on a fixed location, and a sensor in operative communication with the sample capture system, the sensor configured to detect one or more chemical substances excreted from the skin surface of subject.

FIG. 1A shows an embodiment of an apparatus 100 configured to be mounted to a door as part of a door knob. In this illustrative embodiment, the door is an example of a fixed location to which the apparatus 100 can be mounted. Other embodiments for a fixed location will be apparent from the disclosure herein. The apparatus 100 includes a sample capture system 102 configured to be located on a mounting portion 104. The mounting portion 104 can be installed on a fixed location using any means that is known in the art. In the embodiment where the fixed location is a door knob, a shape of the of the mounting portion 104 can thus be configured to be shaped the same as conventional door knobs, which allows the apparatus 100 to be used as both a health sensor as functionally as a door knob. The mounting portion 104 can contain any functional and aesthetic parts required to allow the mounting portion 104 to be attached to a fixed location, such as a door, and be accessible to a subject to serve the normal function that the fixed location would normally perform as well as the enhanced health monitoring disclosed herein.

The apparatus 100 can be manufactured with the sample capture system 102 being separate from the mounting portion 104. For example, in one embodiment, the mounting portion 104 is a conventional door knob and the sample capture system 102 is sold separately and can be placed over the conventional door knob, such that an entire door knob does not have to be refit in order to provide the subject with the health benefits herein. Furthermore, such embodiment may serve to reduce the costs of manufacture, reduce the amount of packaging, and the like. However, in other embodiments, the apparatus 100 can be manufactured with the mounting portion formed integrally with the sample capture system as a whole unit and installed on a door, for example.

In further detail, the sample capture system 102 includes a surface 106 that includes a plurality of pores 108. As described further below, the surface 106 and pores 108 help capture chemical substances of a subject. The sample capture system 102 optionally further includes a suction part 110 configured to operate with the pores 108 to draw in chemical substances through channels (see FIG. 1B). Further, embodiments include that the surface 106 of the sample capture system 102 may include a film (see FIG. 1B). FIG. 1A shows the chemical substances being drawn into and captured by the sample capture system 102 as lines 109, the chemical substances being captured from a subject's contact with the sample capture system 102. The chemical substances are excreted from the subject's skin in sweat and/or sweat vapor or oil excretions.

The sample capture system 102 further includes a sensor 114 configured to perform an analysis on chemicals from discrete sampling events to generate raw data. Although not shown, sensor 114 optionally includes an interface which communicates with a computer 112, such as, but not limited to, a network interface. In one embodiment, the sensor includes processing capabilities to analyze the chemical substances excreted from a subject's skin for a particular sampling event to generate raw data, which can be expressed in one embodiment as a concentration of a particular chemical substance.

In another embodiment, sensor 114 may also include data storage to store one or more of identification information for each subject and raw data generated by the sensor.

The sensor 114 may further include, although not shown, a graphical user interface that can display information such as 1) status of sampling event (such as a red/green/yellow LED light; 2) identification information for each subject; and/or 3) raw data generated by the sensor.

The sensor 114 may further include an input part (not shown) such as, but not limited to, keyboard, touchpad, mouse, joystick, stylus, microphone, and the like, to received input such as, but not limited to, 1) identification information for each subject; and/or 2) user preferences, such as particular chemical substances to be monitored or delivery address for sending raw data, and the like. Of course, some of this information may also be input into a computer 112 instead of the sensor 114.

The computer 112 will be described further below. However, it will be appreciated that the apparatus 100 is optionally communicably connected with computer 112 through wired or wireless connection. For example, the sensor 114 can have an IR, RF, Bluetooth, or other wireless connection that communicates with computer 112. In one embodiment, the sensor 114 may contain additional storage and/or processing capabilities to discern when discrete sampling events have occurred, when concentration of a sampling event is insufficient/sufficient in order to analyze the chemicals properly, as well as communicate subject identification information.

Finally, as shown in FIG. 1A, the apparatus 100 can include a subject verification part 116 to identify the subject to be measured so that the apparatus 100 is able to provide raw data for more than one subject. Subject verification may include the creation of recognition data such as, but not limited to, fingerprint recognition data, optical recognition data such as pupil/iris recognition, facial recognition data, voice recognition data, enzyme recognition data, and the like. (See e.g. Maricialis et al., *Pattern Recognition Letters*, Volume 25, Issue 11, August 2004, Pages 1315-1322; Ong et al., *International Multimedia Conference archive: Proceedings of the 2003 ACM SIGMM workshop on Biometrics methods and applications*, Pages: 100-106, 2003; Amil et al., *Computer Vision and Image Understanding*, Volume 98, Issue 1, April 2005, Pages 104-123).

In the embodiment of FIG. 1A, verification part 116 is a finger print sensor and is located on the surface 106 of the sample capture system 102 so that whenever the apparatus 100 is used (e.g., the door is opened or closed), the finger print sensor obtains identification information to verify which subject touched the apparatus 100. The verification part 116 is shown in FIG. 1A as located on the apparatus 100, but may also be installed separately from the apparatus. For example, in one embodiment, the verification part 116 can be installed on a door higher than the rest of the apparatus 100 and about eye-level to one or more anticipated subjects when the verification part 116 is an eye sensor.

In one embodiment, the verification part 116 can communicate with sensor 114, which sends the identification information to computer 112 along with sampling event information. However, the verification part 116 may also be separately configured to communicate with computer 112 as well.

Figure 1B:
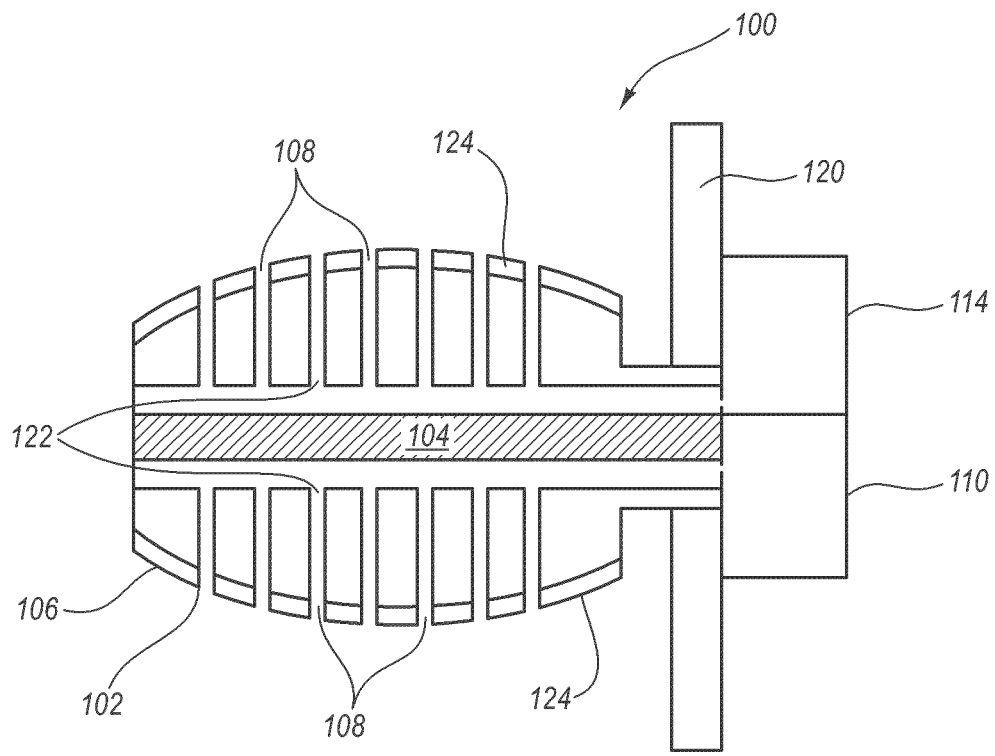
FIG. 1B is a cross-sectional view of the illustrative embodiment of an apparatus of FIG. 1A taken along view x-x'.

FIG. 1B is a cross-sectional view of the apparatus 100 taken along view x-x' of FIG. 1A. FIG. 1B shows apparatus 100 installed on a door 120 as a door knob. That is, the mounting portion 104 is installed on door 120 and the sample capture system 102 is located on the mounting portion 104. FIG. 1B shows in more detail the surface 106 of the sample capture system 102 as well as underneath the surface.

The surface 106 includes a plurality of pores 108. In the embodiment of FIG. 1B, the sample capture system 102 includes channels 122 integrally formed with pores 108 of the surface 106. The pores 108 and channels 122 operate with the optional suction part 110 to suction or draw a chemical substance to the sensor 114 when a subject touches the sample capture system 102. Although not shown, the apparatus 100 may also include a power source to provide power to suction part 110, sensor 114, and/or subject verification part 116, or any other component of apparatus 100 that requires power. Power can be in the form of battery, AC/DC wired, solar power, and the like.

In one embodiment, the diameter of pores may range from about 100 microns to about 10 mm, or about 10 microns to about 10 mm, or about 1 mm to about 10 mm, as illustrative examples. In one embodiment, a density of pores 108 ranges from about 1 to about 10,000 per $cm^2$, or about 1 to 1000 per $cm^2$, or about 1 to 100 per $cm^2$, as illustrative examples. This pore size and density can be designed in any of various configurations to be able to capture a sample of chemicals from a subject's skin efficiently. In one embodiment, the sample capture system 102 is manufactured from any of a combination of metal, metal alloy, plastic, silicon, rubber, ceramic, rock, wood, paper, carbon fiber, and the like.

The channels 122 can have any of various cross sections including, but not limited to, circular, elliptical, square, triangular, or other polygonal shapes. In one embodiment, the channels 122 have the same cross-section as the pores 108. The channels 122 can have a diameter of about 100 microns to about 10 mm, or about 10 microns to about 10 mm, or about 1 mm to about 10 mm, as illustrative examples. The length of the channels 122 will vary depending on how far the corresponding pore 108 is from the sensor 114. The length of the channels can be about 1 cm to about 20 cm, or about 2 cm to about 15 cm, or about 3 cm to about 10 cm, as illustrative examples. The channel 122 can have curved portions or straight portions. In one embodiment, a density of channels 122 ranges from about 1 to about 10,000 per $cm^2$, or about 1 to 1,000 per $cm^2$, or about 1 to 100 per $cm^2$, as illustrative examples. The channel size and density can be designed in any of various configurations to be able to capture a sample of chemicals from a subject's skin efficiently. In one embodiment, the channels can be formed in metal, metal alloy, plastic, silicon, rubber, ceramic, rock, wood, paper, carbon fiber, and the like.

FIG. 1B shows a film 124 formed on the surface 106 of the sample capture system 102. The film 124 can assist to capture chemical substances more efficiently. The film 124 may be formed using various known techniques for thin film processing. In one embodiment, the film may be formed using techniques described in U.S. Pat. No. 5,757,278, incorporated herein by reference. For example, a porous film can be formed of organic material, such as, but not limited to, fluoroplastics, such as PTFE (polytetrafluoroethylene), polycarbonate, cellulose acetate, and the like. In other embodiment, a porous film can be formed of inorganic material such as, but not limited to, metal oxide, metal nitride, metal oxynitride (such as titania and alumina), and the like. In one embodiment, the film 124 captures water from sweat vapor so that less water molecules are delivered to the sensor 114. In another embodiment, the film 124 captures oil from oil excretions so that less oil is delivered to the sensor 114. In addition, to produce an anti-fouling affect, the film 124 may include fluorinated resin coating or photocatalytic materials.

The pores 108 and/or film 124 acquire or capture one or more chemical substances from a subject's skin, which is delivered through channels 122 and carried to sensor 114. Various sensors are known in the art and will not be described in excessive detail to avoid obscuring the invention. For example, an organic substance sensor such as ISSYS FC6 Methanol concentration meter (ISSYS), Micro Motion 7835 Liquid Density and Concentration Meter (Emerson Process Management), or Series 3300 Concentration Analyzer (Kemotron A/S) may be used. Other sensors are also manufactured and can be combined with the apparatuses herein based on the type of chemical substances desired to be analyzed.

As also shown in FIG. 1B, a suction part 110 can be included to deliver the captured chemical substances to the sensor 114 more efficiently. The suction part 110 may be a small fan or a pump and fans/pumps themselves are well known in the art. However, combining the suction part 110 as part of the apparatus provides unique advantages not heretofore known. In addition to effectively delivering the chemical substance to the sensor 114, the suction part 110 also pulls or draws air from outside of the sample capture system 102 through channels 122 between sampling events to effectively "clean out" the pores 108/channels 122 by dispersing the captured chemical substances completely and clean channels 122. Not only does this help avoid contamination in pores 108/channels 122, which can contribute to low accuracy of the monitoring, but also helps keep distinct sampling events more accurate where multiple subjects are being monitored. Other embodiments for clearing out the pores 108/channels 122 include, but are not limited to, a cleansing process such as by using oil or solvent, heating, UV radiation, and the like.

As discussed above, the apparatus 100 can further include a subject verification part 116 (not shown in FIG. 1B) to identify a subject being monitored, giving the apparatus 100 capability to monitor various subjects.

An exemplary apparatus such as that described above can capture various types of chemical substances from a subject's skin using the apparatus. The chemical substances that are sent to the computer 112 can be selected based on the particular subject being monitored, or, alternatively, the sensor 114 can send all raw data of all chemical substances that the sensor is capable of measuring to the computer 112 for analysis. For example, it is known that the concentration of Cl ions increases for subjects having cystic fibrosis or pancreatitis. See Nakakuki et al., SUIZO Vol. 23 (2008), No. 4 pp. 486-493. Further, it is known that the concentration of ammonium or urea increases in subjects having kidney disease. See Huang et al., Chinese Journal of Physiology 45(3): 109-115, 2002. High level of Secretory Immunoglobulin A (S IgA) can be indicative of nephritis, connective tissue disease (CTD), and hepatitis. See http://wapedia.mobi/en/Immunoglobulin_A. Also, it is well known that the concentration of Na ions or K ions increase when people are tired or have a symptom of dehydration. Levels of dermcidin may also be an indicator of the health of a subject. See Shittek et al., Nature Immunology, Vol. 2 no. 12, December 2001. Interleukin-8 (IL-8) and other cytokins are also an indicator of a subject's health. See Murphy, Journal of Leukocyte Biology, Vol. 57, March 1995. Each of these references are incorporated by reference. Thus, examples of chemical substances that can be measured and monitored by sensor 114 include, but are not limited to, chloride, ammonium, urea, sodium, potassium, fatty acids, ketones, IgA, dermcidin, IL-8, leptin, ghrelin, and other cytokins, and the like.

Figure 1C:
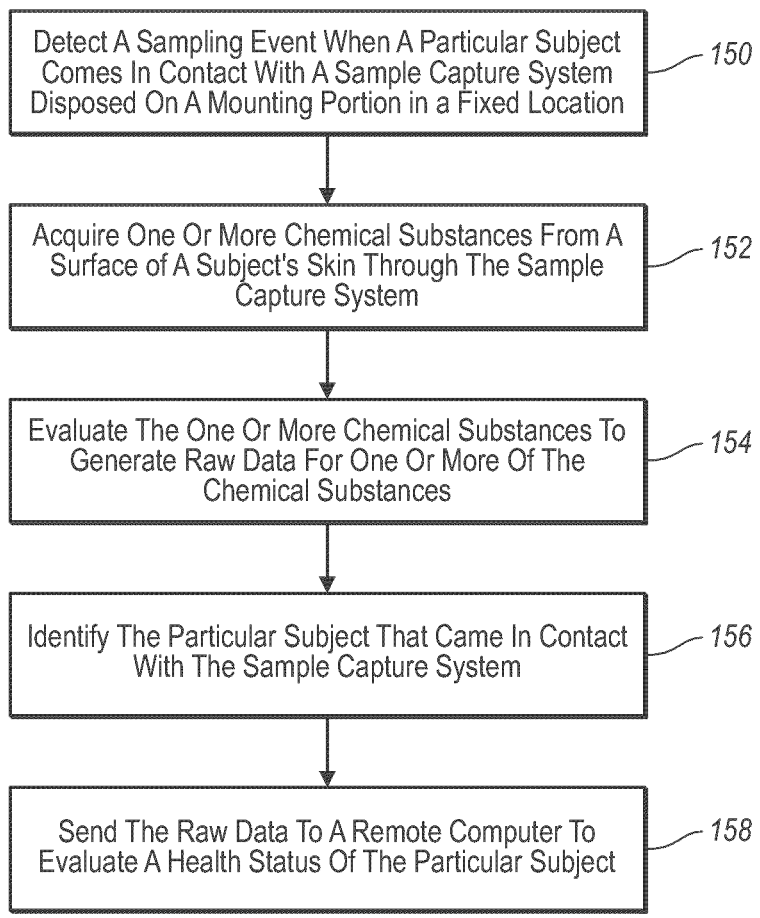
FIG. 1C is a flow diagram of an illustrative embodiment of a method for monitoring a subject's health condition.

FIG. 1C illustrates an example of a method for monitoring a subject's health condition. At 150, when a subject comes in contact with a sample capture system 102 located on a mounting portion 104 in a fixed location, a sampling event begins. A sampling event can be defined in various ways, such as, but not limited to, the subject verification part 116 detecting contact with the apparatus, the sensor 114 detecting an increase or spike in concentration of one or more particular chemical substances after a suction part 110 has cleared out pores and/or channels, detecting usage or interaction with the mounting portion 104 (e.g., in the example of a doorknob, detecting a key inserted into the doorknob, detecting when the doorknob is rotated or turned, and the like).

At 152, the sensor 114 acquires one or more chemical substances from a subject's skin (e.g., in sweat and/or sweat vapor or oil excretions) through the sample capture system. In one embodiment, this can include suctioning the one or more chemical substances through pores 108 and/or channels 122 in the sample capture system 102 toward the sensor 114.

At 154, the sensor 114 evaluates or analyses the acquired one or more chemical substances to generate raw data for one or more of the chemical substance(s). In one embodiment, the raw data can be expressed as a concentration of one or more chemical substances.

Optionally at 156, a subject verification part 116 identifies an identity of the particular subject that came in contact with the sample capture system 102. This can include detecting one or more of fingerprint recognition data, optical recognition data, facial recognition data, voice recognition data, enzyme recognition data, and the like.

At 158, the sensor 114 sends or delivers the raw data and/or subject verification data to a remote computer 112 to evaluate a heath status of the particular subject. It will be appreciated that the sensor 114 can deliver the raw data and/or subject verification data to different computers depending on user preferences for each subject.

Although not shown, the method can also include storing identification information for each subject, raw data generated by the sensor, and the like. The method can also include displaying a status of the sampling event, identification information for the particular subject, raw data generated by the sensor, and the like. The method can further include receiving identification information for each subject, user preferences (such as particular chemical substances to be monitored, delivery address for sending the raw data), and the like. Additionally, the method can include ending the sampling event by drawing air from outside the sample capture system 102 to clear out pores 108 and/or channels 122 in the sample capture system 102.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

Another aspect of the disclosure provides a system for monitoring health of a subject including a computing device having a storage device and a processor and one or more instructions stored on the storage device of the computing device that when executed by the processor on the computing device cause the computing device to evaluate a health condition for a particular subject.

Figure 2A:
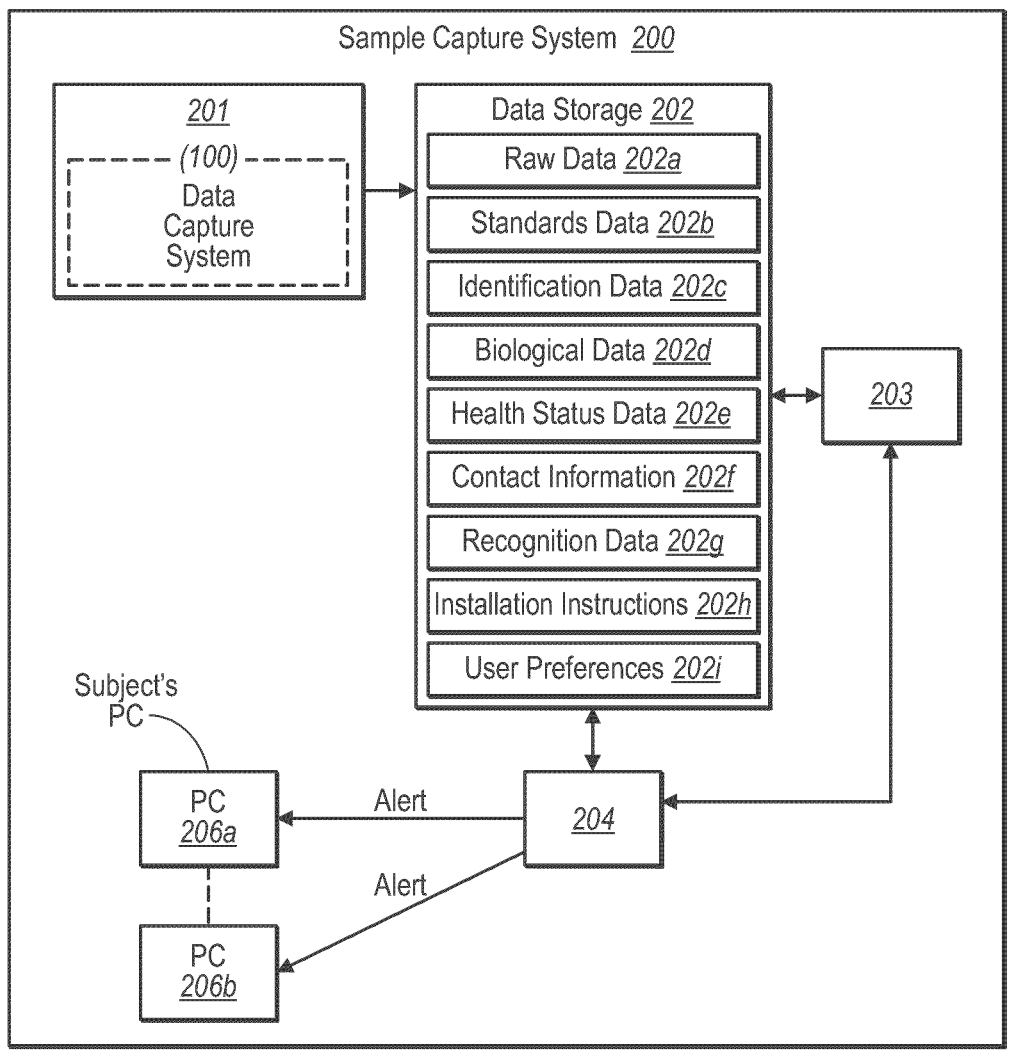
FIG. 2A is a schematic of an illustrative embodiment of a system for monitoring a subject's health condition.

FIG. 2A is a diagram of the system 200 of this disclosure. In one embodiment, the system 200 includes a data capture system 201 to receive raw data for a discrete sampling event for one or more chemical substances that are captured from a subject's skin. In one embodiment, the raw data can be generated by an apparatus installed on a mounting portion of a fixed location (e.g., a doorknob), such as, but not limited to, the apparatus 100 described above. The system 200 also includes a data storage device 202 such as a database or other storage device to store the raw data or any other data received by the data capture system 201.

The data storage device 202 can store various types of data, including, but not limited to, storage for raw data 202a for a discrete sampling event for one or more acquired chemical substances, standards data 202b to hold a standard value of a registered chemical substance (e.g., standard value data of concentration of preregistered chemical substances from various published references), identification data 202c for each subject, biological data 202d for each subject, health status data 202e generated by evaluating the raw data against the standards data and/or biological data for each subject, and the like. The data storage device 202 can also store a history of health status data for one or more subjects. The data storage device 202 can also store contact information 202f for each subject for which health will be monitored. The contact information can contain an address, phone number, fax number, IM address, text message address, voIP address, social networking address, and the like to be able to contact a particular subject when health status data indicates that a concentration of a particular chemical is abnormal, as discussed further below.

The data storage device 202 can further store recognition data 202g such as, but not limited to, fingerprint recognition data, optical recognition data such as pupil/iris recognition, facial recognition data, voice recognition data, enzyme recognition data, and the like. The data storage device 202 can store installation instructions 202h to assist a user in general setup. Further, the data storage device 202 can store user preferences 202i which can specify particular manners for evaluating a subject's health condition and/or manners for conveying information to the subject. For example, the user preferences 202i may specify one or more personal computing devices 206a, 206b for one or more subjects such as, but not limited to, a desktop computer, a mobile device, a personal data assistant, a cell phone, a mini computer, a server-hosted account, and the like, to which to send alerts. User preferences 202i may also specify a frequency of when monitoring is to occur (daily, monthly, etc.), a frequency of maintenance, a frequency of calibration, and the like.

The system 200 includes a processor 203 to evaluate the raw data of each sampling event. In one embodiment, the processor 203 can evaluate the raw data 202a against the standards data 202b for a particular chemical substance to generate health standards data 202e. In one embodiment, the health status data 202e may be expressed as a delta or differential between the raw data and the standards data. In another embodiment, the health status data 202e may be expressed as a grade, degree, or other indicator to reflect the amount that the raw data is above or below the standards data. In some embodiments, the standards data 202b may be enough for the processor to determine health status data 202e of whether the concentration of a particular chemical substance for a particular subject is normal or abnormal.

In other embodiments, the health status data 202e may be more meaningful when considered against the context of the particular person to which the raw data pertains. For example the same concentration for a heavier set person may not have the same significance as it does for a lighter-weight person. Thus, in some embodiments, biological data 202d can be stored for each subject and used when determining the health status data 202e to determine the subject's health condition. For example, the computer 112 may store biological data 202d about a subject such as, but not limited to, height, weight and age of a particular subject. In particular, weight of a subject may be updated periodically using a weight sensor that transmits data to the computer 112. In this embodiment, the processor 203 evaluates the raw data 202a against both the standards data 202 and the biological data 202d for a particular subject to generate health status data 202e based on these additional factors. In this case, the health status data 202e can be expressed as a delta or differential from what a subject having substantially the same biological factors would experience. In another embodiment, the health status data 202e may be expressed as a grade, degree, or other indicator to reflect the amount that the raw data is above or below what a subject having substantially the same biological factors would experience. In some embodiments, standards data 202b may be found that already incorporates biological factors such that a separate analysis using standards data 202b and biological data 202d may not occur; but rather occur in a single analysis.

The system 200 can further include an alert module 204 to send an alert to a computing device for a particular subject in which the health status data 202e indicates that the concentration of a particular chemical substance for that subject is abnormal. The alert module 204 communicates using contact information 202f for a particular subject and/or user preferences for a particular subject.

Figure 2B:
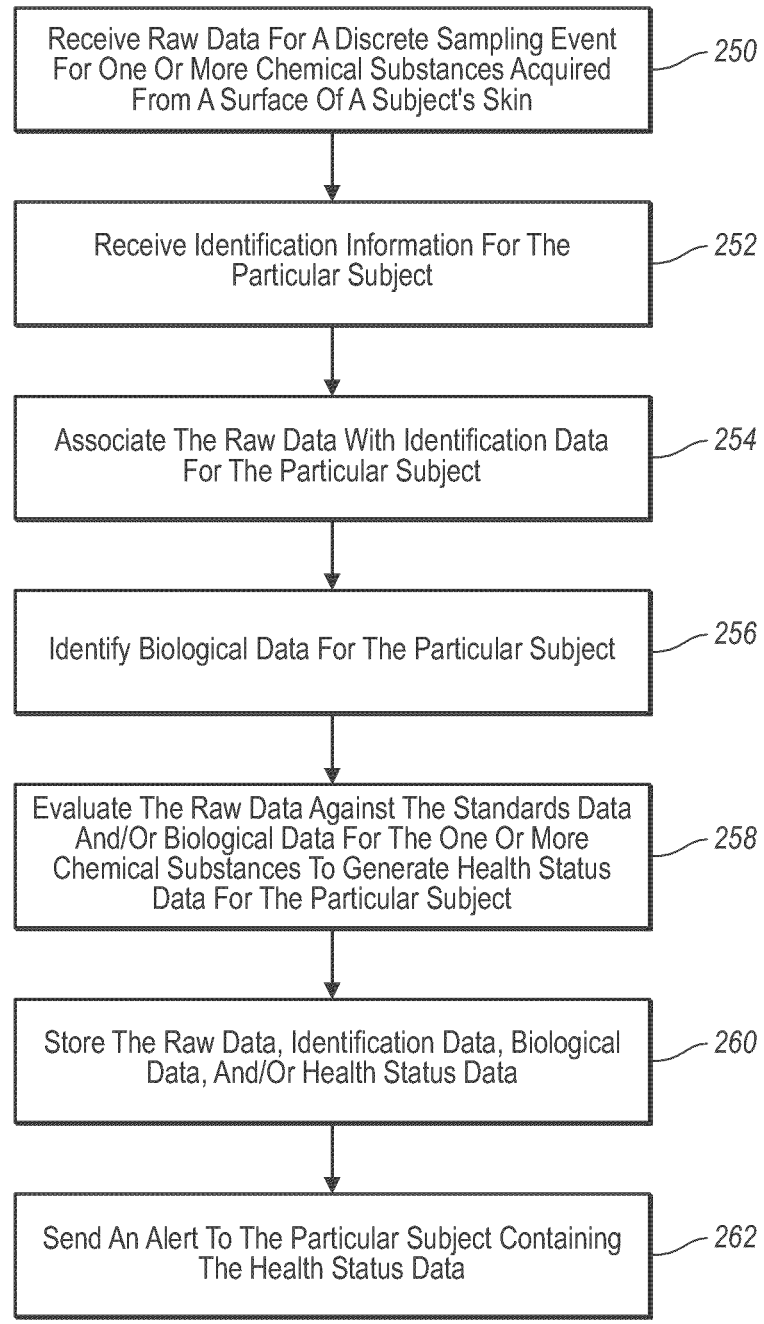
FIG. 2B is a flow diagram of an illustrative embodiment of a method for monitoring a subject's health condition.

FIG. 2B is an example of a method for monitoring a subject's health condition. At 250, the system 200 receives raw data for a discrete sampling event for one or more chemical substances acquired from a subject's skin (e.g., in sweat and/or sweat vapor or oil excretions). The apparatus 100 of this disclosure may be used to acquire the one or more chemical substances and/or generate the raw data, but other various sensor apparatuses may be used as well. For example, the raw data is generated by a sensor 114 located on a mounting portion 104 in a fixed location (e.g., doorknob installed on a door).

Optionally, at 252, the system 200 receives identification information for the particular subject. For example identification information can be generated by a subject verification part 116 associated with a sample capture system 104 installed on a mounting portion in a fixed location and can include, but is not limited to, finger print recognition data, optical recognition data, facial recognition data, voice recognition data, enzyme recognition data, and the like. The identification information received from the apparatus 100 can be compared to identification data 202c stored at the system 200 to identify the particular subject for which the raw data 202a is being received.

However, at 254, generally, the system associates the received raw data 202a with the identification data 202c for the particular subject.

Optionally, at 256, the system 200 can also identify biological data 202d for the particular subject.

At 258, a processor 203 of the system 200 evaluates the raw data 202a against the standards data 202b and/or biological data 202d for the one or more chemical substances to generate health status data 202e for the particular subject.

At 260, the data storage device 202 stores any of raw data 202a, standards data 202b, identification data 202c, biological data 202d, health status data 202e, and/or contact information 202f. In one embodiment, data storage device 202 accumulates data throughout a particular period. For example, the same subject may touch the apparatus 100 frequently in a day. The user preferences stored at the apparatus 100 or at the data storage device 202 may specify for the subject's health to be monitored daily. In one example, the system 200 may store raw data 202a from multiple sampling events throughout the day. At the end of the day, the processor 203 then calculates an average of the raw data for that particular data and uses the averaged value to generate the health status data.

Evaluation of the raw data 202a against the standards data 202b and/or biological data 202d can result in generating a health status data 202e finding that concentration of a particular chemical substance of a subject is lower, higher, or the same as the standard value. The health status data 202e may be reflected as a grade such as, but not limited to, "excellent," "good," "fair," or "poor." At 262, the system 200 uses the contact information 202f to send an alert to the particular subject, the alert containing the health status data. In one embodiment, an alert may be sent only when the health status data indicates that the subject's health is fair or poor.

Although not shown, the method can further include displaying one or more of identification data for each subject, biological data for each subject, raw data generated by the sensor, health status data, and the like. The method can also include receiving input of one or more of installation instructions, user preferences, identification data for each subject, or biological data for each subject.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

As described above, the apparatuses, systems, and methods of this disclosure provide easy, frequent health monitoring. The fixed location on which the apparatus is installed can be any location in which the subject comes into frequent contact. When the fixed location is a doorknob on a door, the subject(s) just uses the apparatus as a door knob, which serves a dual purpose of opening/closing the door as well as passively monitoring the subjects' health. Not only does this provide a low-maintenance solution to monitoring health care, but can also reveal hidden disease that may not be readily ascertainable by a person.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In an illustrative embodiment, any of the operations, processes, etc. described herein can be implemented as computer-readable instructions stored on a computer-readable medium. The computer-readable instructions can be executed by a processor of a mobile unit, a network element, and/or any other computing device.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g. the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g. "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g. "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. An apparatus for monitoring health comprising:
   a doorknob;
   a sample capture system arranged on the doorknob, the sample capture system configured to collect at least some chemicals excreted from a skin surface of a subject during a sampling event, wherein the sample capture system is configured for installation on a fixed location;
   a sensor in operative communication with the sample capture system, the sensor configured to detect one or more chemical substances included in the collected chemicals and generate data regarding the one or more chemical substances;
   a processor in operative communication with the sensor, the processor configured to provide an output in response to the detection of the one or more chemical substances;
   a data storage device operatively coupled with the processor and configured to store the data from the sampling event and configured to store data associated with previous sampling events, wherein the processor determines a health of the subject based on an average of the sampling event and the previous sampling events, wherein the output includes a grade of the health of the subject; and
   a subject verification part configured to verify an identity of the subject by generating recognition data, wherein the recognition data is compared to previously stored identification data to verify the identity of the subject.

2. The apparatus of claim 1, wherein the sample capture system comprises one or more pores formed on a surface of the sample capture system and one or more channels underneath the surface to carry the acquired one or more chemical substances to the sensor.

3. The apparatus of claim 2, wherein the one or more pores have a diameter of about 100 micron to about 10 mm.

4. The apparatus of claim 2, wherein the one or more pores formed on the surface have a density of about 1 pore to about 10,000 pores per $cm^2$.

5. The apparatus of claim 2, wherein the sample capture system comprises one or more channels communicating with the one or more pores to carry the acquired one or more chemical substances to the sensor.

6. The apparatus of claim 2, wherein the sample capture system comprises a suction part to draw the one or more chemical substances through the one or more pores and the one or more channels to the sensor.

7. The apparatus of claim 2, wherein the sample capture system comprises a porous film formed on the surface configured to capture the one or more chemical substances in sweat and/or sweat vapor from the subject's body.

8. The apparatus of claim 7, wherein the porous film is formed form one or more of fluoroplastic, polycarbonate, cellulose acetate, metal oxide, metal nitride, metal oxynitride, fluorinated resin coating or photocatalytic materials, or a combination thereof.

9. The apparatus of claim 1, wherein the subject verification part is configured to obtain identification information for each subject that contacts the sample capture system.

10. An apparatus for monitoring health, the apparatus comprising:
    a doorknob;
    a sample capture system associated with the doorknob, the sample capture system configured to collect a sample from a subject during a sampling event, wherein the sample capture system includes a mounting portion installed on a door, wherein the mounting portion includes a surface having one or more pores formed in the surface leading to channels;
    a sensor configured to detect substances in the sample, wherein the channels are configured to carry the sample to the sensor, wherein the sensor generates data for one or more substances included in the sample; and
    a processor in operative communication with the sensor, wherein the processor receives the data and generates an output related to a status of the subject;
    a subject verification part configured to verify an identity of the subject using recognition data obtained from the subject, wherein the recognition data is compared to previously stored identification data to verify the identity of the subject; and
    a data storage in operative communication with the processor, the data storage configured to store at least the data generated by the sensor and data generated by the sensor from previous sampling events and biological data associated with the subject,
    wherein the output from the processor includes a status of the subject that is based on an evaluation of the data, the data of the previous sampling events, and previously stored biological data,
    wherein the status includes a grade of a health of the subject.

11. The apparatus of claim 10, wherein the one or more pores have a diameter of about 100 micron to about 10 mm.

12. The apparatus of claim 10, wherein the one or more pores formed on the surface have a density of about 1 pore to about 10,000 pores per cm$^2$.

13. The apparatus of claim 10, wherein the sample capture system comprises a suction part to draw the one or more chemical substances through the one or more pores and channels to the sensor.

14. The apparatus of claim 13, wherein the suction part is configured to draw air from outside of the sample capture system through the channels to clean out the one or more pores and the channels.

15. The apparatus of claim 10, wherein the sample capture system comprises a porous film formed on the surface configured to capture the substances in sweat and/or sweat vapor from a body of the subject.

16. The apparatus of claim 15, wherein the porous film is formed form one or more of fluoroplastic, polycarbonate, cellulose acetate, metal oxide, metal nitride, metal oxynitride, fluorinated resin coating or photocatalytic materials, or a combination thereof.

17. The apparatus of claim 10, wherein the subject verification part is configured to obtain identification information for each subject that contacts the sample capture system.

18. The apparatus of claim 10, wherein the output reflects a health of the subject and wherein the output is generated by comparing the data to a predetermined standard.

19. The apparatus of claim 10, wherein the sensor communicates with the processor over a wireless connection, wherein the processor is configured to discern discrete sampling events.

* * * * *

UNITED STATES PATENT AND TRADEMARK OFFICE
CERTIFICATE OF CORRECTION

Page 1 of 1

PATENT NO. : 9,050,061 B2
APPLICATION NO. : 12/550629
DATED : June 9, 2015
INVENTOR(S) : Omoda It is certified that error appears in the above-identified patent and that said Letters Patent is hereby corrected as shown below:

In the specification

In Column 1, Line 44, delete "hereof In" and insert -- hereof. In --, therefor.

In Column 9, Line 27, delete "capture system 104" and insert -- capture system 102 --, therefor.

In Column 9, Line 48, delete "202f In" and insert -- 202f. In --, therefor.

In Column 11, Line 13, delete "thereof In" and insert -- thereof. In --, therefor.

In Column 12, Line 54, delete "(e.g." and insert -- (e.g., --, therefor.

In Column 12, Line 59, delete "(e.g." and insert -- (e.g., --, therefor.

In Column 12, Line 66, delete "(e.g." and insert -- (e.g., --, therefor.

In Column 13, Lines 19-20, delete "thereof In" and insert -- thereof. In --, therefor.

Signed and Sealed this
Ninth Day of August, 2016

Michelle K. Lee
*Director of the United States Patent and Trademark Office*